US006302836B1

(12) United States Patent
North, Jr.

(10) Patent No.: US 6,302,836 B1
(45) Date of Patent: Oct. 16, 2001

(54) METHOD FOR PARTITIONING BLOOD AND DELIVERING CLEAN SERUM

(76) Inventor: Howard L. North, Jr., 100 via Santa Maria, Los Gatos, CA (US) 95030-6334

( * ) Notice: Subject to any disclaimer, the term of this patent is extended or adjusted under 35 U.S.C. 154(b) by 0 days.

(21) Appl. No.: 09/401,463

(22) Filed: Sep. 22, 1999

Related U.S. Application Data

(60) Provisional application No. 60/102,698, filed on Oct. 1, 1998.

(51) Int. Cl.[7] .................................................. B04B 11/00
(52) U.S. Cl. ................................ 494/37; 494/10; 494/27; 494/41; 494/42
(58) Field of Search .............................. 494/5, 6, 10, 19, 494/23, 25, 26, 27, 30, 31, 37, 38, 41, 43, 47, 84, 42, 11; 422/72; 366/213

(56) References Cited

U.S. PATENT DOCUMENTS

| | | | |
|---|---|---|---|
| 3,061,280 | * 10/1962 | Kraft et al. . | |
| 3,159,384 | * 12/1964 | Davis . | |
| 3,190,547 | * 6/1965 | Shanley . | |
| 3,199,775 | * 8/1965 | Drucker . | |
| 3,235,173 | * 2/1966 | Unger . | |
| 3,596,673 | * 8/1971 | Laucournet . | |
| 3,882,716 | * 5/1975 | Beiman . | |
| 4,004,883 | * 1/1977 | Meyer et al. . | |
| 4,555,183 | * 11/1985 | Thomas . | |
| 4,828,716 | 5/1989 | McEwen et al. . | |
| 5,030,341 | 7/1991 | McEwen et al. . | |
| 5,195,825 | * 3/1993 | Ringrose | 366/213 |
| 5,308,506 | 5/1994 | McEwen et al. . | |
| 5,840,253 | * 11/1998 | Chase et al. | 494/41 |

* cited by examiner

Primary Examiner—Charles E. Cooley

(57) ABSTRACT

An ordinary vacuum blood collection tube assembly is rotated about its longitudinal axis to partition a blood sample into serum and formed elements by centrifugation. While still rotating a higher density, immiscible inert liquid is pumped into the vacuum blood collection tube assembly thereby displacing lower density serum towards the axis of rotation and thence out of the vacuum blood collection tube assembly to a serum receiver vessel. A contaminant detector located on the serum delivery conduit controls a 3 way valve to divert contaminants from the removed serum to a waste vessel so only clean serum is delivered to the serum receiver vessel. The serum delivery conduits, serum cannula, and contaminant detector are washed and dried between successive samples to limit sample carryover effects to acceptably low levels. These operations may be fully automated so a carousel of blood samples may be processed sequentiall to deliver clean serum to a second carousel of serum cups without operator intervention at the rate of about one sample per minute.

10 Claims, 7 Drawing Sheets

METHOD FOR PARTITIONING BLOOD AND DELIVERING CLEAN SERUM

Figure 1:
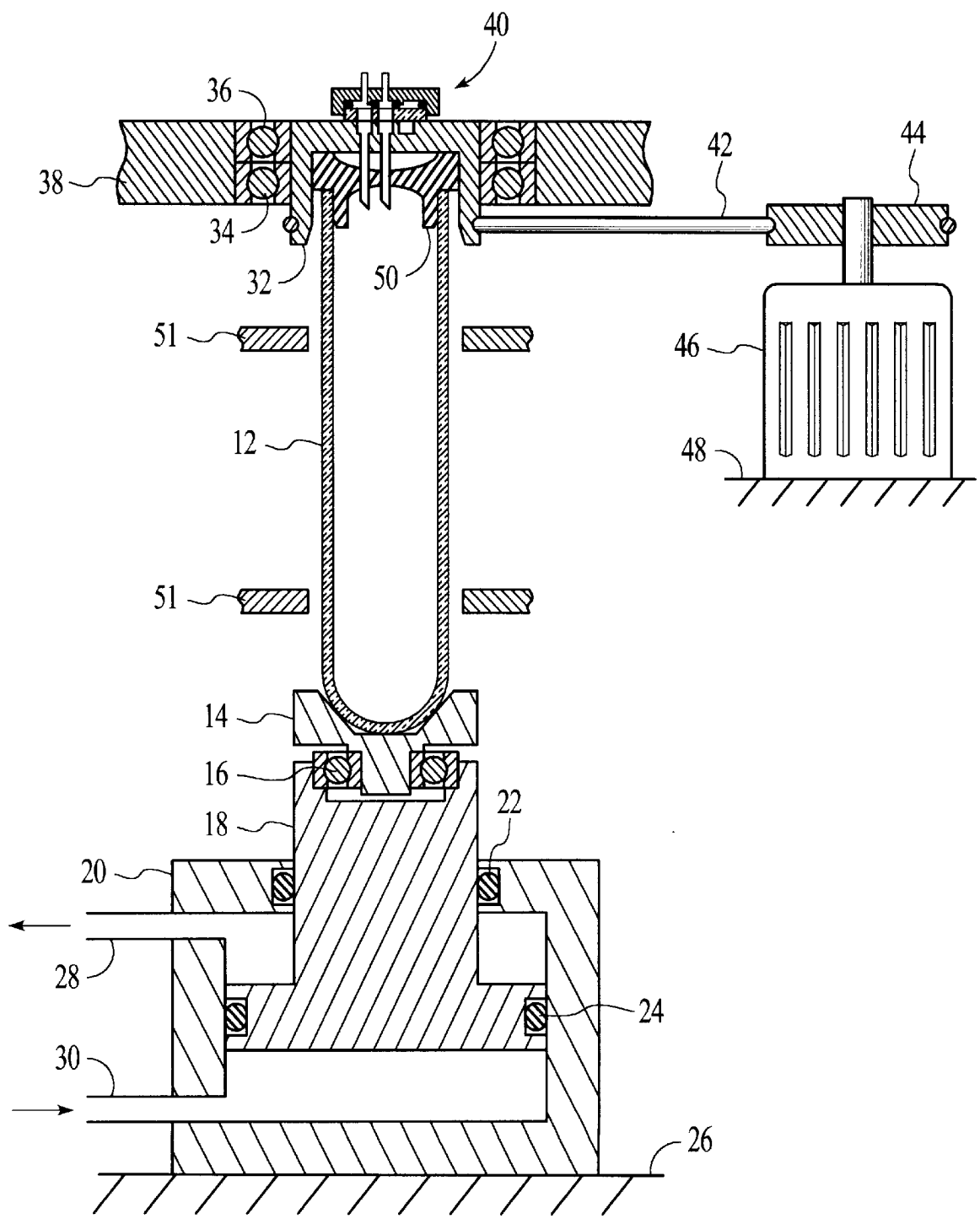

This application Ser. No. 09/401,463 filed Sep. 22, 1999 is based on provisional patent application No. 60/102,698 filed Oct. 1, 1998.

This is a substitute specification.

BACKGROUND—FIELD OF INVENTION

This invention relates to a method for partitioning a blood sample and obtaining clean serum from an unopened vacuum blood collection tube assembly.

BACKGROUND—DESCRIPTION OF PRIOR ART

Hospital clinical laboratories often analyze blood serum for various chemical constituents by using automated analyzers. The blood is first drawn from a patient into a vacuum blood collection tube assembly. After the blood clots this tube is placed in a centrifuge which causes the clot material to move to the end of the tube away from the tube stopper. The less dense serum is then between the clot material and the tube stopper.

Serum is then removed from the tube and presented by various methods to a blood serum chemistry analyzer. One method requires removal of the stopper and removal of the serum by pipetting or decanting the serum into a serum cup from which serum is dispensed to an analyzer. These operations may be manual or automated or a mixture of these methods.

Serum may be removed from an unopened vacuum blood collection tube assembly following centrifugation without removal of the stopper by piercing the elastomeric stopper with a cannula so that the distal end of the cannula is fully immersed in serum. Serum is then aspirated from the tube via the cannula by a syringe or pump and delivered to a serum cup or an analyzer. These operations may be manual or automated or a mixture of these methods.

Various apparatus have been constructed to automate the operations of separating serum from the clot by centrifugation, removal of the stopper, and removing and dispensing of serum. Automation of centrifugal separation of serum and clot using conventional centrifuges has proven to be complex and costly due to the large number of separate operations required. These include the following:
(a) removing the blood tube from a carousel or rack
(b) placing the blood tube in a centrifuge rotor
(c) repeating (a) and (b) for a number of blood tubes
(d) balancing the centrifuge rotor
(e) closing the centrifuge lid
(f) rotating the centrifuge rotor for a predetermined time and speed sufficient to separate serum from the clot
(g) stopping the centrifuge rotor
(h) opening the centrifuge lid
(i) removing each tube from the centrifuge rotor
(j) placing each blood tube in a carousel or rack suitable for subsequent operations of serum removal and dispensing.

These operations have proven to be difficult to automate economically rendering this approach of limited value.

In an effort to more readily automate the centrifugation step McEwen et al in U.S. Pat. No. 5,308,506 issued May 3, 1994 employ the method of rotating the vacuum blood collection tube assembly about its longitudinal axis. This method thus avoids most of the above (a) through (j) steps. However, McEwen et al then employ a slidable piston positioned within the vacuum blood collection tube assembly during centrifugation to preserve the separation of serum and clot after rotation of the blood tube ceases. McEwen et al also use a special device, shown on FIG. 8 of his patent, to remove and dispense serum from an unopened vacuum blood collection tube assembly. Removal of serum from an unopened vacuum blood collection tube assembly is highly desirable since it avoids biohazardous aerosols sometimes generated by removal of the blood tube stopper. These aerosols have caused infections with HIV and hepatitis.

The McEwen invention suffers from the following shortcomings which have limited its utility:

1. It requires a special vacuum blood collection tube assembly containing a slidable piston which adds cost to the blood tube. It also adds more work and the need for more storage space in the laboratory stockroom.
2. It requires a special device to remove serum from an unopened vacuum blood collection tube assembly which adds cost to the process since the special device must either be disposable or must be washed after each use to avoid sample carryover problems. It also adds more work and the need for more storage space in the laboratory stockroom if disposable.
3. It requires a special centrifuge apparatus to rotate the vacuum blood collection tube assembly about its longitudinal axis.
4. The operations of serum separation by centrifugation, serum removal, and serum dispensing are all separate operations not easily automated and integrated. They thus require manual interventions which lead to significant time and labor costs.
5. There is no provision for the removal from the dispensed serum contaminants such as air, microclots, and cellular aggregates which can cause malfunction of automated serum chemistry analyzers.

OBJECTS AND ADVANTAGES

Accordingly, in addition to avoiding many of the shortcomings of the McEwen invention, further objects and advantages of the present invention are;

(a) to provide an apparatus and method which fully automates and integrates the operations of separation of serum from clots, removal of serum from an unopened vacuum blood collection tube assembly, and dispensing of removed serum to a remote receiver vessel.

(b) to provide the operations of (a) while using a standard, unmodified vacuum blood collection tube assembly without any special features such as an enclosed slidable piston (c) to provide the operations of (a) without requiring any one time use or disposable device (d) to provide the operations of (a) and delivering clean serum free from contaminants such as air, microclots, cellular aggregates, or fibrin strands (e) to provide clean serum from an unopened vacuum blood collection tube assembly including the operations of separating serum from the clot, removing and cleaning serum, and dispensing a metered volume of serum in less than one minute (f) to provide the operations of (e) with significantly less cost for labor and materials than conventional methods (g) to provide the operations of (e) without use of devices requiring disposal (h) to provide for the washing and drying of reusable serum conduits to reduce sample carryover to acceptable levels (i) to provide means for dispensing a predetermined volume of clean serum from an unopened vacuum blood collection tube assembly to a remote receiver vessel.

Other objects and advantages will become apparent from a consideration of the ensuing description and drawings.

DRAWING FIGURES

Figure 2:
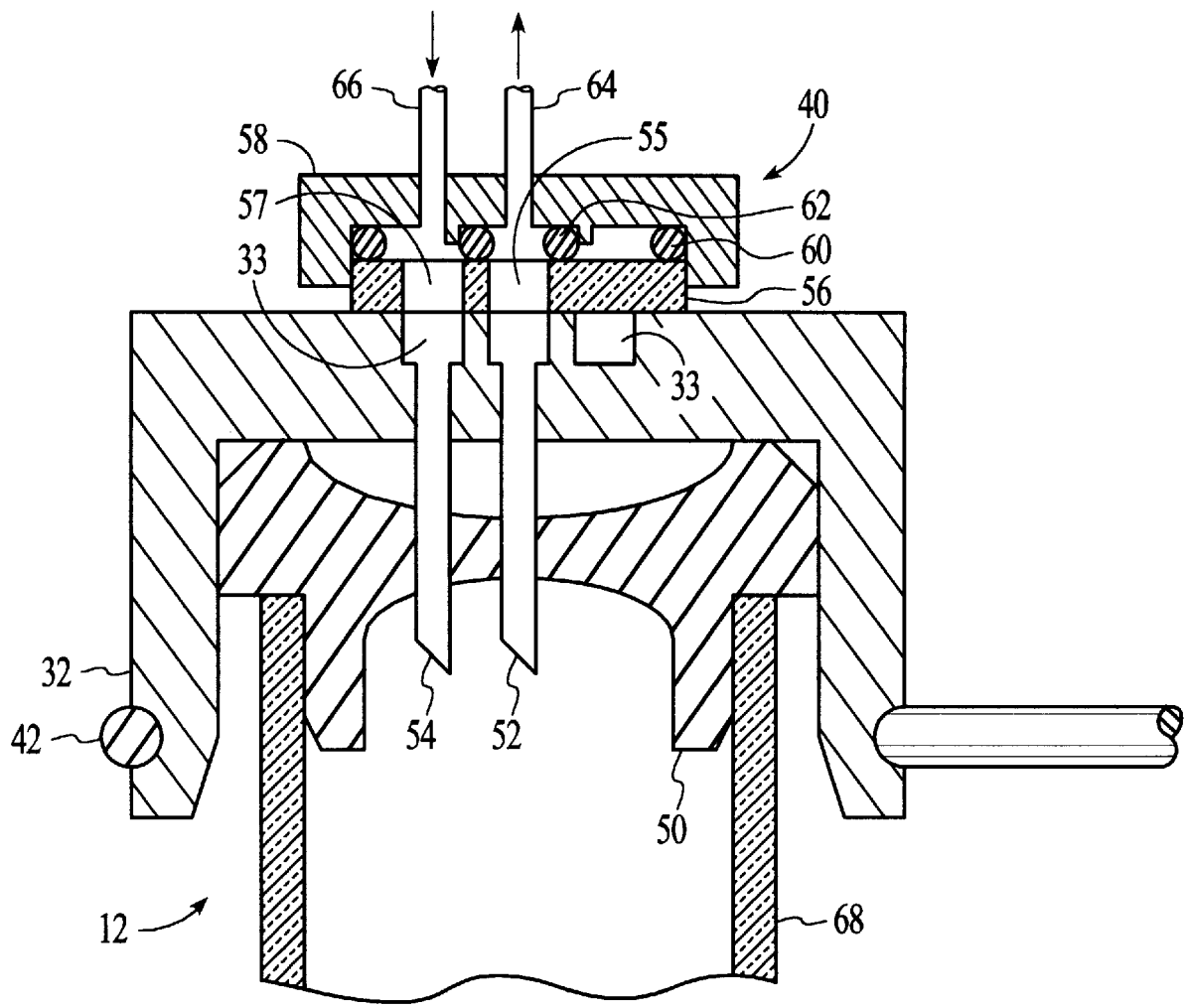
Figure 3:
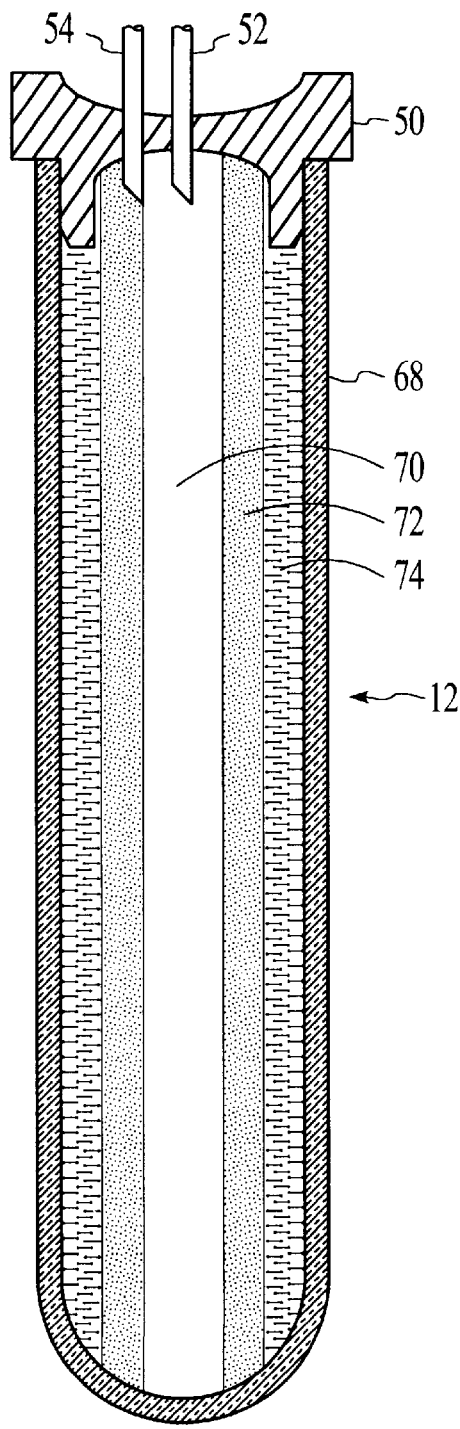
Figure 4:
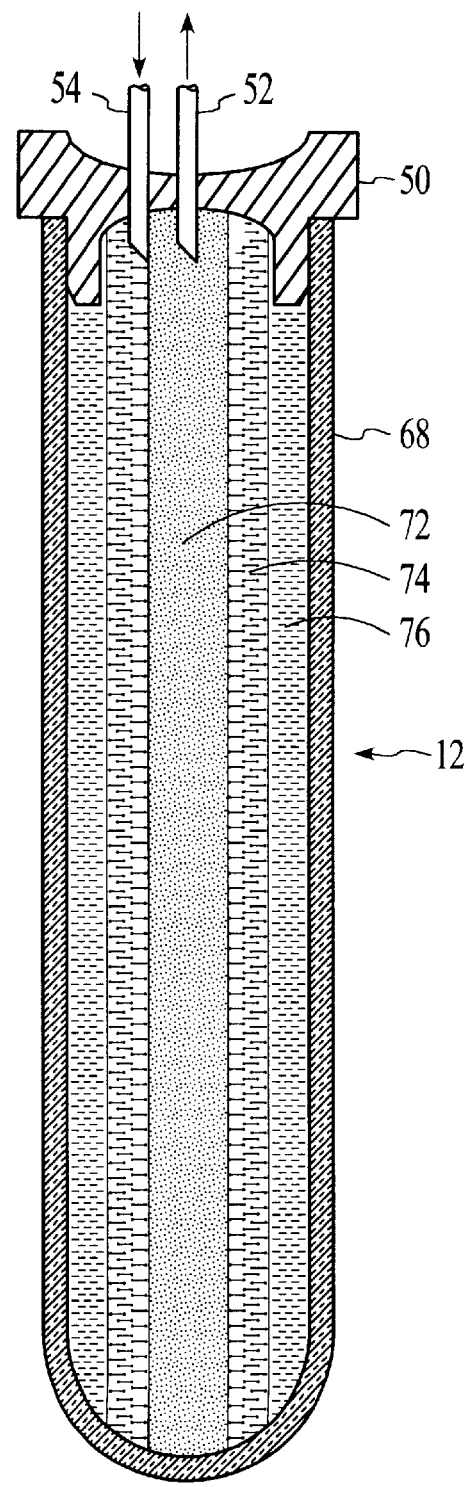
Figure 5:
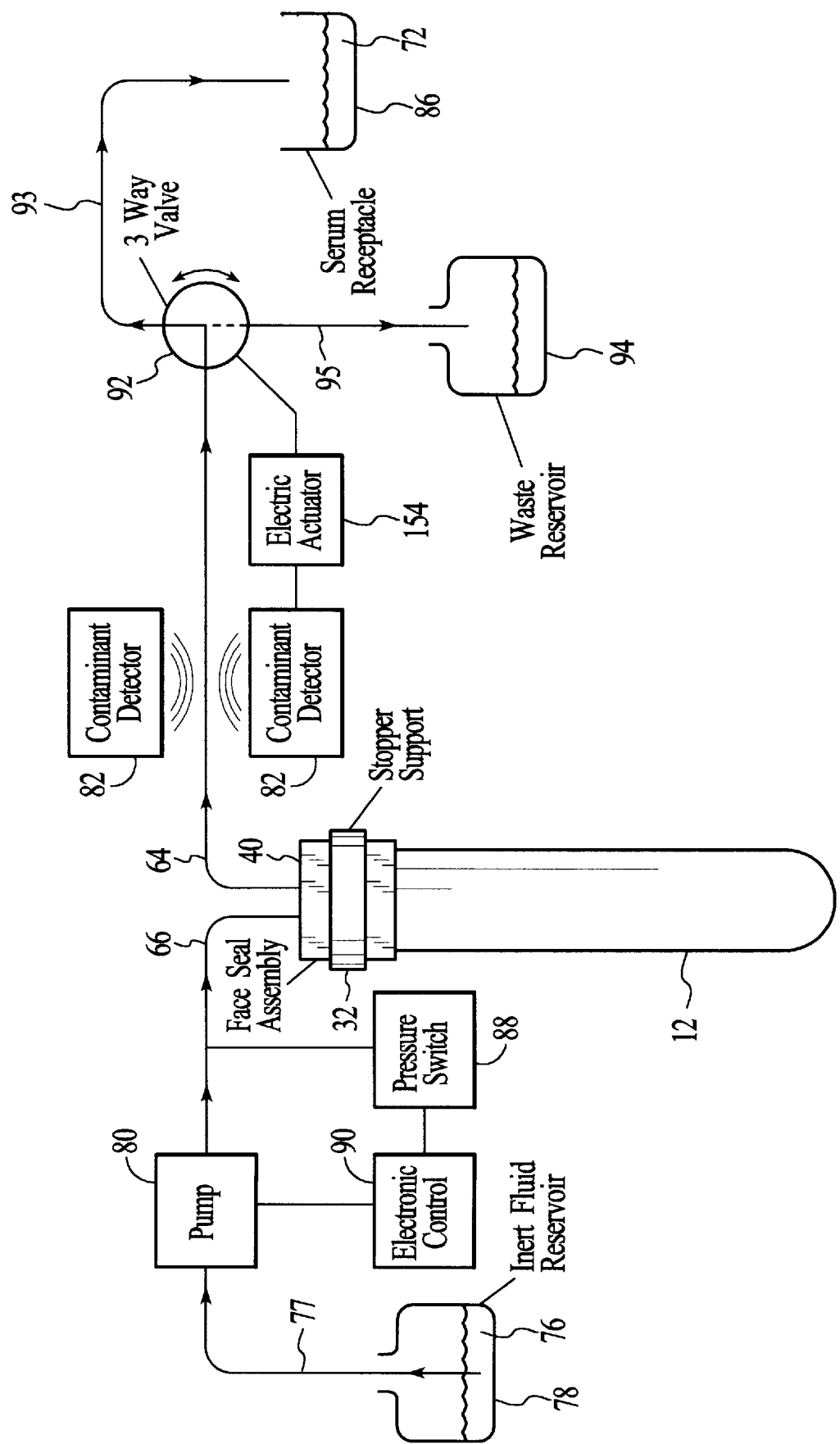
Figure 6:
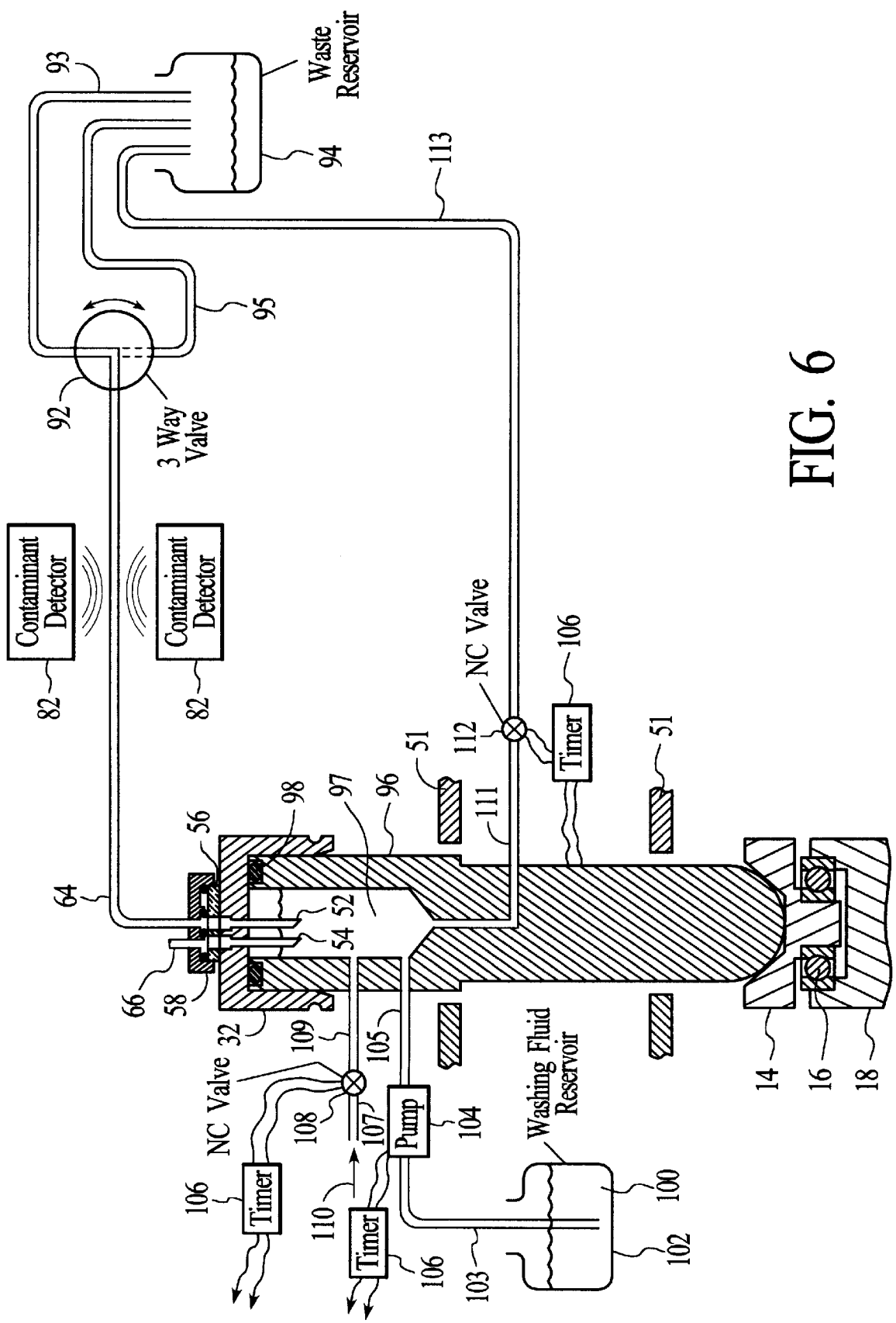
Figure 7:
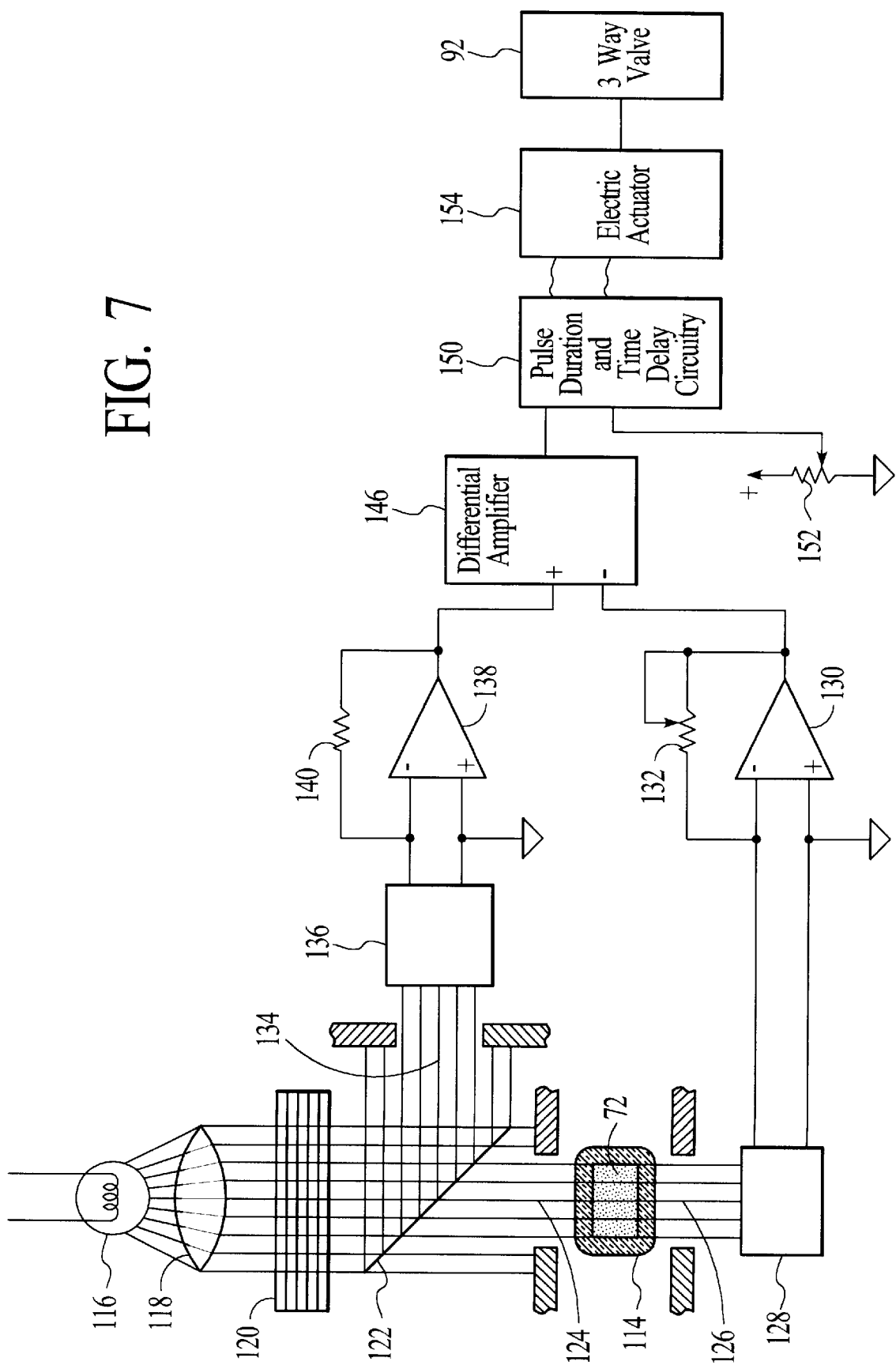
Figure 8:
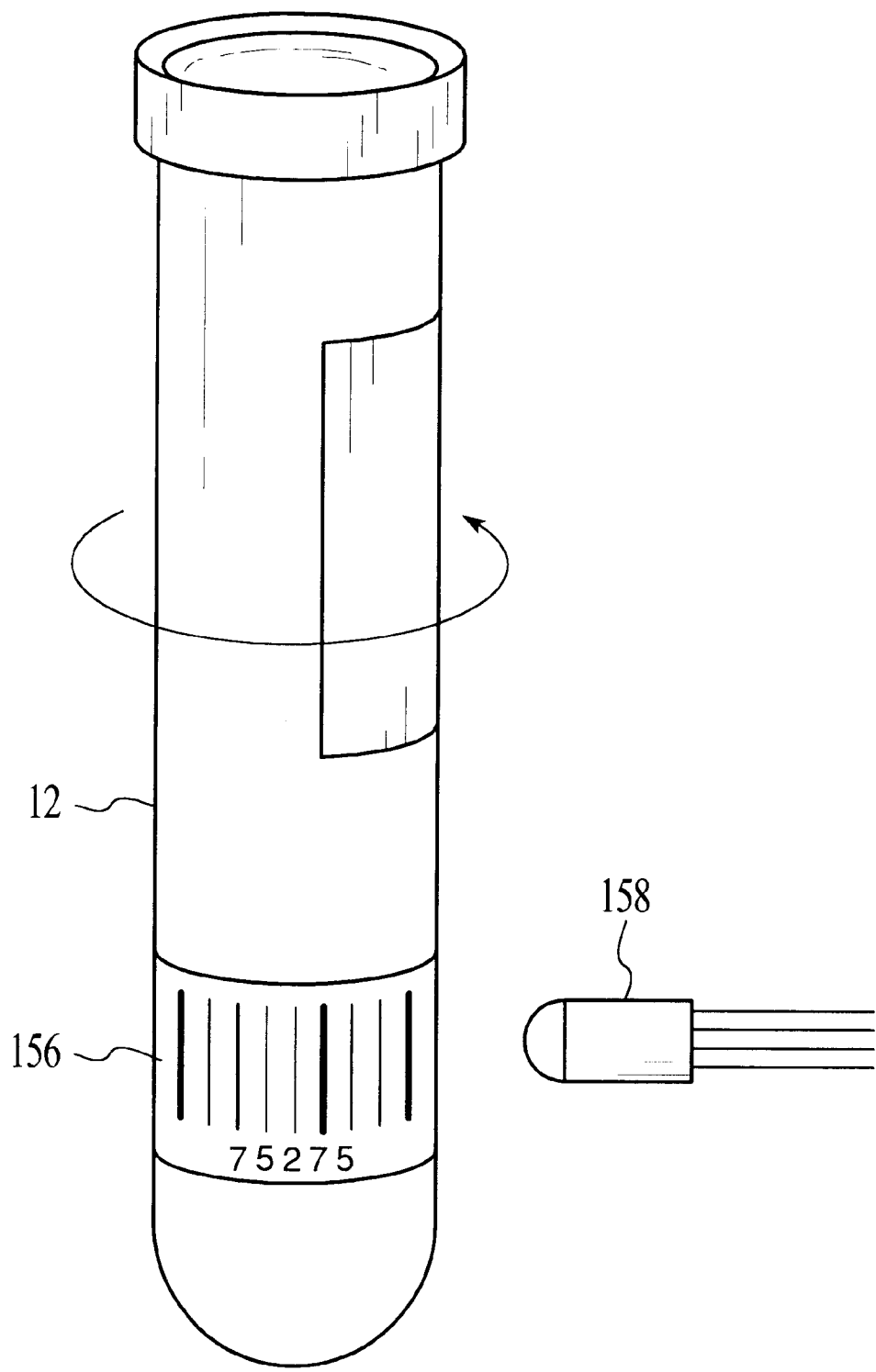

FIG. 1 shows a vacuum blood collection tube assembly, supports, and rotational drive FIG. 2 shows cannulae penetrating the stopper and a face seal assembly FIG. 3 shows positions of serum and formed elements after centrifugation FIG. 4 shows positions of serum, formed elements, and inert fluid during serum expulsion FIG. 5 is a fluid schematic for serum expulsion and cleaning FIG. 6 is a fluid schematic for washing and drying serum conduits FIG. 7 is a schematic for a contaminant detector and valve control FIG. 8 shows a sample identification reader

DESCRIPTION—FIGS. 1 THROUGH 8

Referring to FIG. 1 item 12 is a vacuum blood collection tube assembly containing a clotted blood sample and some residual air. Item 51 is a rotary carousel containing a plurality of tube assemblies. Item 14 is a tube support having a conical surface mating with item 12 and connected to a bearing 16 located in a piston 18 which slides in a cylinder 20 and is sealed thereto by seals 22 and 24. Cylinder 20 is supported by stationary structure 26 and is connected to a conventional source of compressed air and ambient air by valves (not shown) to ports 28 and 30. A stopper support 32 engages a stopper 50 and is supported by bearings 34 and 36 in stationary structure 38. Stopper support 32 is rotated by motor 46 mounted on stationary structure 48, pulley 44, and drive belt 42 and is in contact with face seal assembly 40.

Referring to FIG. 2 serum cannula 52 and an inert fluid cannula 54 are integral with stopper support 32 and are penetrating through elastomeric stopper 50 which is the closure for vacuum blood collection tube 68. Face seal assembly 40 is comprised of a face seal 56 containing holes 55 and 57 which are sealed to a face seal holder 58 by O-rings 60 and 62 thus providing communication with the interior of vacuum blood collection tube assembly 12 through serum cannula 52, hole 55, and serum conduit 64 and also through inert fluid cannula 54, annular groove 33, hole 57, and inert fluid conduit 66.

Referring to FIG. 3 rotation of vacuum blood collection tube assembly 12 about its longitudinal axis has caused higher density formed elements 74 to be centrifuged against vacuum blood collection tube 68 with lower density serum 72 on top of the formed elements 74. Residual air 70 inside vacuum blood collection tube assembly 12 occupies the location nearest the axis of rotation due to its extremely low density.

Referring to FIG. 4 rotation of vacuum blood collection tube assembly 12 about its longitudinal axis has caused a high density inert fluid 76, introduced via inert fluid cannula 54, to be centrifuged against the inner wall of vacuum blood collection tube 68. To obtain this condition the inert fluid density must be higher than the density of the formed elements or higher than about 1.09 gram/cubic centimeter. When the density of the inert fluid is greater than the density of serum but less than the density of the formed elements partitioning of the serum from the formed elements still occurs but the positions of inert fluid 76 and formed elements 74 in FIG. 4 would be exchanged. Inert fluid 76 should dissolve very little of the analyte chemicals in serum 72 to avoid altering the concentration of analytes in serum 72. Since the analytes are generally water soluble inert fluid 76 must have a low solubility of water in it. Also inert fluid 76 must have a high purity to avoid altering serum 72 and should have a boiling point high enough to avoid boiling problems. A suitable inert fluid 76 is a perfluorocarbon liquid such as FC-70 Fluorinert manufactured by 3M Company. At 25 C. this liquid has a density of 1.94 gram/cubic centimeter, boiling point of 275 C., surface tension with water of 18 dyne/centimeter, and solubility of water of 8 parts per million. FC-70 Fluorinert may be too expensive if not recovered for reuse. Lower cost liquids which may be satisfactory are trichloroethylene, tetrachloroethylene, n-butyl phthalate, Dow Corning phenylmethylpolysiloxane oils DC560 and DC710, and Dow Corning fluorosilicone oil FS1265. Going back to FIG. 4 formed elements 74 and serum 72 are displaced radially inwards by inert fluid 76 and serum 72 is brought into contact with serum cannula 52.

Referring to fluid schematic FIG. 5 inert fluid 76 from inert fluid reservoir 78 flows through conduit 77 to the inlet of pump 80 which is a reversible positive displacement pump such as a peristaltic tubing pump. The outlet of pump 80 communicates with an inert fluid conduit 66 and a pressure switch 88 connected to an electronic control which regulates pump 80. Inert fluid conduit 66 introduces inert fluid 76 into vacuum blood collection tube assembly 12. Serum conduit 64 removes serum from vacuum blood collection tube assembly 12. A contaminant detector 82 is located in serum conduit 64 and operates electric actuator 154 to position a 3 way valve 92 which connects serum conduit 64 either to a serum delivery conduit 93 or to a waste conduit 95. 3 way valve 92 is a zero dead volume type to minimize loss of serum. Serum delivery conduit 93 is positioned with its delivery end over a serum receptacle 86. Serum 72 in serum receptacle 86 is then presented to a serum analyzer by conventional means (not shown) for analysis.

Referring to FIG. 6 item 96 is a washing tube which has replaced vacuum blood collection tube assembly 12 by rotation of carousel 51. A washing fluid reservoir 102 provides washing fluid 100 via conduit 103 to pump 104 controlled by timer 106. The outlet of pump 104 is connected via conduit 105 to a cavity 97 inside washing tube 96. A conventional source of compressed air (not shown) 110 delivers air via conduit 107 to a normally closed valve 108 controlled by timer 106 and thence via conduit 109 to cavity 97. An 0-ring 98 seals washing tube 96 to stopper support 32. The bottom of cavity 97 is connected to waste reservoir 94 via conduit 111, a normally closed valve 112 controlled by timer 106, and conduit 113.

Referring to FIG. 7 a tungsten filament lamp 116 has a lens 118 which focuses a beam of light through a band pass filter 120, a beam splitter 122, an aperture 124, a transparent flow cell 114 containing serum 72, an aperture 126 to a silicon PIN photodiode 128. Photodiode 128 is connected to an operational amplifier 130 having a feedback potentiometer 132. Some light from beamsplitter 122 passes through aperture 134 to a silicon PIN photodiode 136 connected to an operational amplifier 138 having a feedback resistor 140. The outputs of amplifiers 130 and 138 are connected to a differential amplifier 146. A threshold setting potentiometer 152 is connected to a fixed positive voltage and also to a conventional pulse duration and time delay circuitry means 150 (details not shown) which in turn is connected to electric actuator 154 which positions 3 way valve 92.

Referring to FIG. 8 a machine readable marking 156, such as a bar code label, is affixed to vacuum blood collection tube assembly 12 and aligned with an optical identification sensor 158.

GENERAL PRINCIPLES OF OPERATION

A vacuum blood collection tube assembly containing clotted blood is rotated about its longitudinal axis at a speed in the order of 10,000 to 20,000 RPM for a time sufficient for separation of serum from formed elements, usually less than half a minute. While still rotating an inert fluid of high density, immiscible with the blood phases, is introduced into the vacuum blood collection tube assembly which displaces the serum radially inwards towards the axis of rotation due to centrifugal forces. A cannula on the axis of rotation permits the escape of first the air and secondly the serum itself through a delivery conduit to a serum receptacle. A contaminant detector in the serum delivery conduit senses the presence of air, microclots, cellular aggregates, and fibrin strands and diverts them to a waste reservoir thus delivering only clean, bubble free, serum to the serum receptacle for analysis.

After delivery of serum the vacuum blood collection tube assembly is replaced by a washing tube by rotation of a carousel and the serum delivery conduit is moved to a position over a waste reservoir by conventional means (not shown). Then wash fluid is pumped through the serum conduits to expel serum followd by dry compressed air to expel wash fluid and dry the serum conduits. The system is now ready to process another blood sample following return to a vacuum blood collection tube assembly and to a serum receptacle. A bar code label on the outside of each vacuum blood collection tube assembly and a bar code reader provide identification of each blood sample while serum is being expelled and the vacuum blood collection tube assembly is rotating.

SPECIFIC OPERATION

A plurality of vacuum blood collection tube assemblies 12 are loaded manually into a rotary carousel 51 which aligns them one at a time with tube support 14 and stopper support 32. A pressurized fluid, such as air, is applied to port 30 of a cylinder 20 while port 28 is exposed to a lower pressure. Piston 18 rises and lifts bearing 16, tube support 14, and vacuum blood collection tube assembly 12, which is then no longer supported by carousel 51, but is lifted into engagement with stopper support 32 which results in cannulae 52 and 54 penetrating through stopper 50. A motor 46 is energized which rotates stopper support 32 and vacuum blood collection tube assembly 12 via pulley 44 and drive belt 42. Stopper support 32 rotates inside bearings 34 and 36 supported in stationary structure 38.

The blood sample inside vacuum blood collection tube assembly 12 is thus subjected to centrifugal forces in the order of 1000 g's. Formed elements 74, consisting of red and white cells and platelets, some of which are enmeshed in a network of fibrin strands, are forced to the inner diameter of vacuum blood collection tube assembly 68 as shown on FIG. 3. This is due to the formed elements having a density in the order of 1.09 gram/cubic centimeter and the serum having a density in the order of 1.03 gram/cubic centimeter. Air 70 with a density of about 0.001 gram/cubic centimeter thus occupies the inner cylindrical volume inside the vacuum blood collection tube assembly 12. Air 70 is at atmospheric pressure due to venting to the ambient air pressure via serum cannula 52, contaminant detector 82, 3 way valve 92, and serum delivery conduit 93.

An inert fluid 76 is now pumped from an inert fluid reservoir 78 through conduit 77 by pump 80 and then through inert fluid conduit 66, face seal assembly 40 with hole 57, annular groove 33, and inert fluid cannula 54 into the rotating vacuum blood collection tube assembly 12. Inert fluid 76 inside vacuum blood collection tube assembly 12 rapidly moves to the position shown on FIG. 4 and displaces the formed elements 74 and serum 72 radially inwards. Continued pumping of inert fluid 76 into the vacuum blood collection tube assembly 12 causes expulsion of air 70 and then serum 72 out through serum cannula 52, a hole 55 and face seal assembly 40, serum conduit 64, contaminant detector 82, 3 way valve 92, and serum delivery conduit 93 into serum receptacle 86. Serum 72 in serum receptacle 86 may then be used for analysis.

In the event serum cannula 52 is obstructed by formed elements 74 the discharge pressure of pump 80 rises and actuates pressure switch 88 which, operating through electronic control 90, stops pump 80, reverses pump 80 for a brief period of time in the order of one second, and then causes normal pumping to resume. Reversal of pump 80 withdraws material obstructing serum cannula 52 after which normal pumping resumes.

In the event contaminant is detected by contaminant detector 82 3 way valve 92 is operated by electric actuator 154 to a position to divert the contaminant from serum delivery conduit 93 to waste conduit 95 and thence to waste reservoir 94. The operation of 3 way valve 92 is delayed from the time contaminant is first detected by contaminant detector 82 for a period of time slightly less than the time required for the contaminant to flow from contaminant detector 82 to 3 way valve 92. 3 way valve 92 is operated for a minimum period of time in the order of 0.1 second plus an additional period of time equal to the time that contaminant is being detected by the contaminant detector 82. This timing prevents contaminant from being delivered to the serum receptacle 86 while a small amount of serum preceding and following the contaminant is lost to waste reservoir 94.

Contaminant detector 82 is basically a dual beam colorimeter where one light beam is a sample beam and a second light beam is a reference beam. This allows for some light source degradation or changes in photodetector sensitivity due to changes in ambient air temperature or other factors while preserving the accuracy of the colorimeter. A light at about 530 nanometers is used for sensitive detection of clots which contain many red blood cells since the hemoglobin in red blood cells has a high light absorption at 530 nanometers.

Light from a tungsten filament lamp 116 is focused by a lens 118 into apertures 124 and 134 after being passed through a band pass filter 120 and a beam splitter 122. Light into aperture 134 forms the reference beam which is detected by a silicon PIN photodiode 136. The photon induced current from silicon photodiode 136 is input to operational amplifier 138 configured with a feedback resistor 140 to form a transimpedance amplifier whereby the current from silicon PIN photodiode 136 is converted into a proportional voltage at the output of operational amplifier 138.

Light passing through aperture 124 passes through flow cell 114 containing serum 72 and then through aperture 126 into silicon PIN photodiode 128. Aperture 126 prevents light scattered by the corners of flow cell 114 from reaching silicon PIN photodiode 128. The photon induced current from silicon PIN photodiode 128 is input to an operational amplifier 130 configured with a feedback potentiometer 132 to form a transimpedance amplifier. Potentiometer 132 is adjusted so that the voltage outputs of operational amplifiers 130 and 138 are equal when flow cell 114 is full of normal serum 72 and no contaminant is present in flow cell 114. When contaminants such as air, clots, cellular aggregates, or fibrin strands are present in flow cell 114 some of the light passing through flow cell 114 is blocked. Then less current is sent by silicon PIN photodiode 128 to operational amplifier 130 and the output voltage of operational amplifier 130 decreases.

Differential amplifier 146 is a voltage difference amplifier. Thus when the output voltage of operational amplifier 130 becomes less than the output voltage of operational amplifier 138 the output voltage of amplifier 146 moves in a positive direction.

This positive voltage from amplifier 146 is input to a conventional pulse duration and time delay circuitry means 150 which compares this input voltage to a threshold voltage set by a potentiometer 152. When the threshold voltage from potentiometer 152 is exceeded by the output voltage from differential amplifier 146 then pulse duration and time delay circuitry means 150 is triggered to produce a fixed output voltage which is delayed a fixed time and which has a duration equal to the time during which the input voltage exceeds the threshold voltage plus a fixed time duration in the order of 0.1 second. The output voltage of pulse duration and time delay circuitry means 150 operates electric actuator 154 which positions 3 way valve 92 to the position where the output flow from contaminant detector 82 is diverted to waste reservoir 94.

Pump 80 is operated for a predetermined period of time to produce a predetermined volume of serum 72 in the serum receptacle 86. This predetermined period of time is the time it takes pump 80 to deliver the predetermined volume of serum 72 and also fill an empty conduit 64 from contaminant detector 82, 3 way valve 92, and delivery conduit 93. This predetermined time does not include the time 3 way valve 92 is positioned to deliver contaminant to waste reservoir 94.

Following delivery of a predetermined volume of serum 72 to serum receptacle 86 rotation of vacuum blood collection tube assembly 12 is stopped. Piston 18 is lowered by applying high pressure to port 28 and low pressure to port 30 of cylinder 20. Vacuum blood collection tube assembly 12 is pushed off serum cannula 52 and inert fluid cannula 54 and lowered onto support by carousel 51 by suitable conventional means (not shown). Carousel 51 is then rotated by conventional means (not shown) so washing tube 96 is aligned with stopper support 32. Piston 18 is raised by high pressure to port 30 and low pressure to port 28 of cylinder 20. This causes washing tube 96 to be sealed to stopper support 32 by O-ring 98. At the same time that carousel 51 is aligning washing tube 96 with stopper support 32 serum conduit 93 is moved so its exit end is over waste reservoir 94 by conventional means (not shown).

Compressed air is admitted briefly to cavity 97 in washing tube 96 through a conduit 107, a normally closed valve 108 controlled by a timer 106, and conduit 109. This air travels through serum cannula 52, hole 55 and face seal holder 58, serum conduit 64, contaminant detector 82, 3 way valve 92, and serum delivery conduit 93 expelling serum therefrom into waste reservoir 94. Next washing fluid 100 from washing fluid reservoir 102 is delivered by conduit 103, pump 104, and conduit 105 for a predetermined period of time controlled by timer 106 into cavity 97 of washing tube 96. Washing fluid 100 then passes through cannula 52, hole 55 and face seal holder 58, serum conduit 64, contaminant detector 82, 3 way valve 92, and serum delivery conduit 93 thereby washing out most of the residual serum 72. Next compressed air 110 from a conventional source is admitted into cavity 97 in washing tube 96 through conduit 107, a normally closed valve 108, and conduit 109. Valve 108 is energized open by timer 106 for a predetermined period of time sufficient to expel substantially all of the residual washing fluid 100 and then to substantially dry the interiors of serum cannula 52, hole 55 and face seal holder 58, serum conduit 64, contaminant detector 82, 3 way valve 92, and serum delivery conduit 93.

Initially, when compressed air 100 is introduced into cavity 97 in washing tube 96, air bubbles are formed which rise to the surface of washing fluid 100. This provides some washing of the external surfaces of cannulae 52 and 54. Shortly after opening normally closed valve 108 a normally closed valve 112 is opened by timer 106 for a predetermined period of time sufficient to substantially empty cavity 97 of washing fluid 100 via conduit 111, normally closed valve 112, and a conduit 113.

Inert fluid cannula 54 will normally be filled with inert fluid 76. Any serum 72 or washing fluid 100 which may be present inside the open end of inert fluid cannula 54 just prior to expulsion of washing fluid 100 from cavity 97 ma be expelled by operating pump 80 briefly to discharge a small volume of inert fluid from inert fluid cannula 54 thereby purging inert fluid cannula 54 of any residual serum 72 or washing fluid 100.

At any time vacuum blood collection tube assembly 12 is rotating a machine readable marking 156 may be scanned by an optical identification sensor 158 to provide sample identification information to an automated serum analyzer.

This method for obtaining clean, uncontaminated serum from an unopened vacuum blood collection tube assembly may also be used to obtain clean, uncontaminated plasma when the blood sample is anticoagulated. Operation is unchanged. The foregoing descriptions apply except the word "plasma" replaces the word "serum" and the words "formed elements" replace the word "clot".

SUMMARY, RAMIFICATIONS, AND SCOPE

Accordingly, the reader will see that the method herein described provides for the removal of serum or plasma from a blood sample contained in an unopened vacuum blood collection tube assembly. Furthermore, this method provides the following advantages over methods of the existing art:
- it provides easy automation of the entire process of partitioning a blood sample and delivering a particular phase to a remote receiver vessel without manual intervention
- it avoids biohazardous conditions by not opening vacuum blood collection tube assemblies it avoids biohazardous conditions by not requiring manual handling of blood or its components it reduces the cost for this process by not requiring manual intervention it reduces the cost for this process by the use of a standard, unmodified vacuum blood collection tube assembly it reduces the cost for this process by not requiring additional apparatus or devices for the removal and dispensing of the removed blood phase following centrifugal partitioning of the blood phases.

it provides for the removal from a removed blood phase of contaminants such as air, microclots, cellular aggregates, or fibrin strands which can cause malfunction of serum or plasma analyzers it provides for the accurate and precise delivery of a volume of a removed phase to a receiver vessel.

Although the description above contains many specificities, these should not be construed as limiting the scope of the invention but as merely providing illustrations of some of the presently preferred embodiments of this invention. For example, the vacuum blood collection tube assembly can be rotated about other than a vertical axis and by means other than an electric motor and a drive belt such as by an air motor or by gears or by means integral with the tube support. The air operated piston and cylinder used to lift the vacuum blood collection tube assembly could be operated by hydraulic fluid or be replaced by an electrical linear actuator means. The optical contaminant detector could be replaced by an electronic detector sensing the change in impedance in a conduit caused by the presence of contaminant.

The method is applicable when plasma or other blood components are to be removed from an unopened vacuum blood collection tube assembly or when materials other than blood components are to be separated and removed from a closed cylindrical chamber.

The operations of washing and drying the conduits carrying a removed blood component may be omitted when carryover from one sample to the next is not important. Similarly, the operations of detecting the presence of contaminant in the removed component and removing the contaminant by diverting it to a waste container may be omitted when such contaminant removal is not required. Metering of the volume of the removed component may be omitted when such metering is not important.

Thus the scope of the invention should be determined by the appended claims and their legal equivalents, rather than by the examples given.

What is claimed is:

1. A method for partitioning and removing from a chamber a preselected phase of a sample of liquid, comprising the steps of: containing in an elongated cylindrical closed chamber having a substantially constant cross-sectional area a sample of said liquid having a plurality of phases of different densities and having a total liquid volume less than that of said chamber, and ordering said sample phases concentrically by rotating said chamber about its longitudinal axis, wherein the improvement comprises:

(a) increasing the volume of said liquid in said chamber, while said chamber is rotating and said phases are ordered, by introducing into said chamber through a first rotary seal and a first cannula an inert liquid immiscible with said sample phases and having a density greater than the density of the highest density sample phase to be removed, and (b) continuing to introduce said inert liquid, thereby forcing any residual gas and at least one of said sample phases out of said chamber via a second rotary seal and a second cannulalocated substantially on the longitudinal axis of said chamber, whereby said sample phases are removed from said chamber in the order of their densities with the lowest density sample phase being removed first.

2. A method as described in claim 1 wherein said chamber is a vacuum blood collection tube assembly closed by an elastomeric stopper, said cannulae pierce said elastomeric stopper, said sample is anticoagulated blood, and said sample phase first removed is serum.

3. A method as described in claim 1 wherein said chamber is a vacuum blood collection tube assembly closed by an elastomeric stopper, said cannulae pierce said elastomeric stopper, said sample is anticoagulated blood, and said sample phase first removed is plasma.

4. A method as described in claim 3 wherein a second phase removed consists primarily of platelets, a third phase removed consists primarily of leukocytes, and a fourth phase removed consists primarily of erythrocytes.

5. A method of metering the volume of a phase of sample delivered from a partitioned sample of liquid, comprising the steps of containing in an elongated cylindrical closed chamber having a substantially constant cross-sectional area a sample of liquid having a plurality of phases of different densities and having a total volume less than that of said chamber and ordering said sample phases concentrically by rotating said chamber about its longitudinal axis, wherein the improvement comprises:

(a) while said chamber is rotating and said phases are ordered, increasing the volume of liquid in said chamber by introducing into said chamber via a first rotary seal and a first cannula an inert liquid immiscible with said sample phases and having a density greater than the density of the lowest density sample phase to be removed, and (b) continuing to introduce said inert liquid, thereby forcing out any residual gas and the lowest density phase of said sample from said chamber via a second rotary seal and a second cannula located substantially on the longitudinal axis of said chamber, and (c) predetermining the volume of said lowest density phase of said sample delivered from said chamber by predetermining the volume of said inert liquid being introduced into said chamber during delivery of said lowest density phase of said sample from said chamber, whereby a predetermined volume of said lowest density phase of said sample is delivered from said chamber both accurately and precisely.

6. A method as described in claim 5 wherein said chamber is a vacuum blood collection tube assembly closed by an elastomeric stopper, said sample is coagulated blood, and said sample phase removed is serum.

7. A method as described in claim 5 wherein said chamber is a vacuum blood collection tube assembly closed by an elastomeric stopper, said sample is anticoagulated blood, and said sample phase removed is plasma.

8. A method as described in claim 5 further including the step of predetermining the volume of said lowest density phase of said sample delivered from said chamber by predetermining the volume of said inert liquid delivered from an inert liquid reservoir into said chamber by a positive displacement pump during delivery of said lowest density phase of said sample.

9. A method as described in claim 8 further including the step of predetermining the volume of said inert liquid delivered into said chamber by said positive displacement pump by predetermining the time of operation of said positive displacement pump.

10. A method as described in claim 8 further including the steps of:

(a) monitoring the discharge pressure of said positive displacement pump, and (b) stopping operation of said positive displacement pump whenever said discharge pressure exceeds a predetermined maximum value, and (c) reversing the flow from said positive displacement pump for about one second, whereby excessive discharge pressure of said positive displacement pump is prevented and obstructing material at the entry of said second cannula is removed by reverse flushing, and (d) resuming original operation of said positive displacement pump.

\* \* \* \* \*